United States Patent [19]

Roof

[11] 4,070,913

[45] Jan. 31, 1978

[54] SAMPLE DILUTION

[75] Inventor: Lewis B. Roof, Bartlesville, Okla.

[73] Assignee: Phillips Petroleum Company, Bartlesville, Okla.

[21] Appl. No.: 719,217

[22] Filed: Aug. 31, 1976

[51] Int. Cl.$^2$ .............................................. G01N 1/10
[52] U.S. Cl. ................. 73/422 GC; 137/604; 366/136; 366/177
[58] Field of Search ......... 73/421 R, 422 GC, 61.1 C, 73/23.1; 259/4 R; 137/604

[56]  References Cited
U.S. PATENT DOCUMENTS 3,712,144  1/1973  Kuzel et al. ....................... 73/421 R
3,976,429  8/1976  Ginsberg ........................... 73/421 R Primary Examiner—S. Clement Swisher

[57] ABSTRACT

Two conduit means having a preselected volumetric relationship one to the other are utilized in the dilution of a sample by filling one of the conduit means with a diluent liquid and the other with a sample material, then connecting the two conduit means together in a closed conduit loop and circulating the contents of the loop through the loop in order to cause uniform mixing of the sample material with the diluent liquid. In a preferred embodiment the diluted sample material is resampled from the conduit loop for further use or analysis.

15 Claims, 1 Drawing Figure

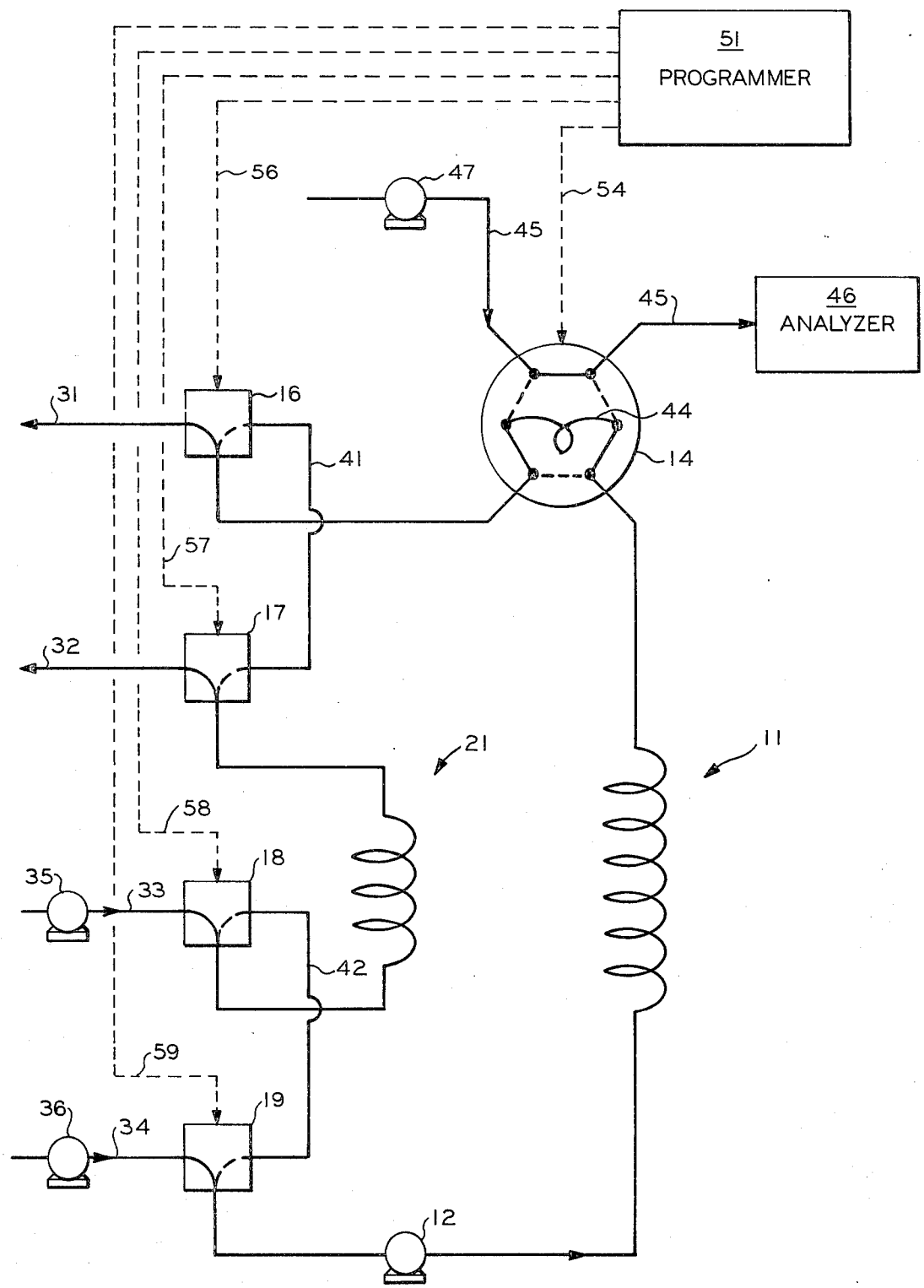

SAMPLE DILUTION

This invention relates to an apparatus and method for diluting a sample. In another aspect the invention relates to an apparatus and method for diluting a sample material using a liquid diluent. In yet another aspect the invention relates to an apparatus and method for automatic dilution of a sample material. In still another aspect the invention relates to an apparatus and method for diluting a sample by continuously circulating preselected volumes of sample material and diluent liquid around a closed conduit loop.

Samples to be analyzed, particularly those to be analyzed by process liquid chromatography or laboratory liquid chromatography often require dilution prior to analysis. Dilution is ordinarily used to regulate some property of the sample mixture to aid the analysis. For example, the boiling point of the sample can be regulated to prevent solidification or vaporization, the total quantity used for analysis of the sample can be reduced to below that normally available by using a sample injection valve alone, or the viscosity of the sample can be reduced to provide better sample flow through the analysis instrument. In addition to dilution of samples to be analyzed by liquid chromatography, dilution of samples for other purposes is likewise often desirable.

It is particularly desirable to provide an automatic sample dilution system suitable for use with high viscosity samples such as polymers or rubbers which either cannot be analyzed by liquid chromatography in an undiluted state or which require extremely high temperature analyzer operation in order to permit analysis without dilution.

Accordingly, an object of the invention is to provide an apparatus and method for diluting a sample. Another object of the invention is to provide an apparatus and method for diluting a sample material using a liquid diluent. Yet another object of the invention is to provide an apparatus and method for automatic dilution of a sample material. Still another object of the invention is to provide an apparatus and method for diluting a sample by continuously circulating preselected volumes of sample material and diluent liquid around a closed circuit loop. Another object of the invention is to provide an apparatus and method for diluting high viscosity samples.

In accordance with the invention an apparatus and method are provided whereby a first conduit means having a first volume is filled with a diluent liquid and a second conduit means having a volume bearing a predetermined size relationship to the volume of the first conduit means is filled with a sample material. The first and second conduit means are then connected in series to form a closed conduit loop and the contents of the conduit loop are circulated around the loop to cause mixing of the diluent liquid and sample material. The diluted sample material in the conduit loop can then be resampled for analysis or for any other purpose for which a diluted sample is desired. After the desired use is made of the diluted sample material the first and second conduit means can be returned to their initial condition so that diluent liquid can be flushed through the first conduit means and sample material can be flushed through the second conduit means in order to obtain fresh diluent liquid and sample material for use in a subsequent dilution procedure.

Additional objects and advantages of the invention will be apparent from the description thereof and the appended claims thereto, as well as from the detailed description of the drawing in which the sole FIGURE is a schematic representation of a preferred sample dilution system embodying the apparatus and method of the invention.

Referring to the FIGURE there is illustrated a first conduit means 11, including a pump means 12 and associated portions of a sample valve means 14, connected at its first end to a first valve means 16 and at its second end to a fourth valve means 19. A second conduit means 21 is connected at its first end to a second valve means 17 and at its second end to a third valve means 18. Each of the valve means 16, 17, 18, and 19 is a two-way valve permitting the establishment of fluid communication between the respective associated conduit end and either of two additional conduit means. Each of the valve means 16, 17, 18, and 19 therefore has a first position schematically illustrated in the FIGURE by the solid line through the box representing the valve, and a second position schematically illustrated in the FIGURE by the dashed line through the box representing the respective valve.

When each of the valve means 16, 17, 18, and 19 is in its respective first position as illustrated by the FIGURE, the first valve means 16 establishes fluid communication between the first end of the first conduit means 11 and a diluent disposal conduit 31; the second valve means provides fluid communication between the first end of the second conduit means 21 and a sample disposal conduit 32; the third valve means 18 provides for fluid communication between the second end of the second conduit means 21 and a sample supply conduit 33; and the fourth valve means 19 provides for fluid communication between the second end of the first conduit means 11 and a diluent supply conduit 34. When each of the valve means 16, 17, 18, and 19 is in its illustrated first position, therefore, diluent liquid flows through the diluent supply conduit 34, through the fourth valve means 19, and into the second end of the first conduit means 11. The diluent liquid then proceeds through the conduit means 11 through the second end thereof, into the first valve means 16, and from the first valve means 16 into the diluent disposal conduit 31. At the same time, sample material flows through the sample supply conduit 33 and the third valve means 18 into the second end of the second conduit means 21, through the second conduit means 21 to the first end thereof, and then continues through the second valve means 17 into the sample disposal conduit 32. While the sample supply conduit 33 and diluent supply conduit 34 can be provided with appropriate pump means 35 and 36 respectively in order to insure a flow of sample material and diluent liquid to the third valve means 18 and fourth valve means 19 respectively, such pump means 35 and 36 or equivalent means for initiating flow through their respective supply conduits may not be necessary in applications where sufficient process or reservoir pressure is available to insure supply conduit flow. In addition, the pump means 12 located in the first conduit means 11 can be used under appropriate conditions to provide flow through the diluent supply conduit 34 and fourth valve means 19 into the first conduit means 11.

After a period of time sufficient for the flow of diluent material through the first conduit means 11 and sample material through the second conduit means 21 to displace and flush any material remaining from a previous dilution in either of the conduits through the associated disposal conduits 31 and 32 and for the first conduit means 11 and second conduit means 21 to be filled with fresh diluent liquid and sample material respectively, the valve means 16, 17, 18, and 19 are substantially simultaneously switched to their respective second positions. With the valves in their respective second position the first valve means 16 provides fluid communication between the first end of the first conduit means 11 and the first end of a first connecting conduit 41; the second valve means 17 provides fluid communication between the first end of the second conduit means 21 and the second end of the first connecting conduit 41; the third valve means 18 provides fluid communication between the second end of the second conduit means 21 and the first end of a second connecting conduit 42; and the third valve means 19 provides fluid communication between the second end of the first conduit means 11 and the second end of the second connecting conduit 42. In this configuration the first end of the first conduit means 11 and the first end of the second conduit means 21 are connected through the first connecting conduit 41, and the second end of the first conduit means 11 and second end of the second conduit means 21 are connected through the second connecting conduit 42 to provide a closed loop containing the diluent liquid of the first conduit means 11 and the sample material of the second conduit means 21. Continued actuation of the pump means 12 to provide continuing circuitous circulation of the contents of the closed loop is then used to mix the contents of the closed loop until a uniformly diluted sample material is obtained. Circulation through the closed loop can be maintained for as long as necessary to provide a uniformly diluted sample material mixture therein, with the exact time required for each specific apparatus configuration being dependent upon the relative volume of the loop, the speed and capacity of the pump means 12, the solubility and mobility of the sample material in the diluent liquid, the turbulence of flow through the conduit loop, and other similar parameters.

The volumes of the first connecting conduit 41 and second connecting conduit 42 are preferably so much smaller than the volume of either the first conduit means 11 or second conduit means 21 that the minute amount of diluted sample material remaining therein from the immediately preceding dilution procedure has an insignificant or negligible effect on the composition of any subsequent diluted sample. As a practical matter such connecting conduits 41 and 42 will ordinarily be no more than a coupling connecting one valve directly to another or, in any of the numerous equivalent apparatus configurations available, a short internal passageway in a double or multiple valve. However, in some applications such as the monitoring of process streams in which substantial rapid changes in sample material will not occur, the volume of the connecting conduits 41 and 42 can be greater, without causing any significant alteration of subsequent sample composition, than they can under similar circumstances in a process where it is important to immediately recognize small and rapidly changing variations in sample material content.

After a period of time sufficient for thorough mixing of the sample material and diluent liquid in the closed conduit loop, the sample valve 14 may be used to inject a preselected volume of sample material from the sample loop 44 thereof into the flow of chromatographic carrier liquid through an analyzer input conduit 45 to a chromatographic analysis means 46. The analyzer input conduit 45 and analysis apparatus 46 can be any suitable liquid chromatographic analysis apparatus or, in the case of a sample which is eluted to provide increased volatility, could be a suitable gas chromatographic analysis apparatus in which the diluted sample material is vaporized to present a gaseous sample to the analysis means 46 for analysis. Although a pump means 47 is illustrated providing chromatographic carrier fluid flow, any suitable means for establishing such flow can be used.

In order to provide for automatic unattended dilution and sampling of successive portions of sample material, a suitable programming means 51 is provided to generate valve actuating signals 54, 56, 57, 58, and 59 to actuate respective valve means 14, 16, 17, 18, and 19 in a preselected time relationship. As previously indicated, valve means 16, 17, 18, and 19 are preferably simultaneously changed from their illustrated first position (solid lines) to their second position (dashed lines) in order to connect the first conduit means 11 and second conduit means 21 in a series relationship. While the sample valve means 14 is schematically illustrated in a first position (solid lines) wherein the sample loop 44 is included in the first conduit means 11, the size and characteristics of the sample loop 44 may be such that it is desirable to avoid passage of sample material therethrough until it has been completely diluted, and the sample valve means 14 may be maintained in its second position (dotted lines) until after sample material dilution has been accomplished.

When the complete dilution of the sample material has been accomplished and a uniform diluted sample material mixture is contained within the closed conduit loop, the sample valve means 14 is switched to its illustrated first position, if not already in that position, to permit the sample loop 44 to fill with the diluted sample material. After a period of time sufficient for the sample loop 44 to be flushed and filled with diluted sample material, the sample valve means 14 is placed in a second position to inject the sample contained within the sample loop 44 into the flow of material through the carrier conduit 45. After injection of the sample into the analysis system or other use of the diluted sample has been completed, all valves are returned to their initial position for initiation of a subsequent dilution cycle.

While the specific apparatus embodiment of the invention best suited for each particular application can vary widely, it has been found that for use with standard chromatographic analysis equipment the first and second conduit means 11 and 21 can advantageously be constructed from conduit having an inside diameter of at least about 0.2 inch (standard ¼-inch outside diameter tubing) when use of the system to dilute and lower the viscosity of a particularly viscous sample is desired. Likewise, it is preferred that the paths of fluid communication associated with the pumps and valves incorporated into the apparatus of the invention be large enough to permit the desired circulation of sample material and diluent liquid around the conduit loop to be maintained. If desired, a portion of either the conduit means 11 or conduit means 21 can be of a larger inside diameter than the remainder of these conduit means in order to promote more rapid mixing of the sample material with the diluent. Presently preferred apparatus for use in implementing the preferred embodiment of the invention illustrated by the FIGURE for diluting a viscous rubber or polymer sample is as follows:

| | |
|---|---|
| First conduit means 11 | 1/4 in. O.D. 10 ft. long stainless steel |
| Second conduit means 21 | 1/4 in. O.D. 3 in. long stainless steel |
| Pump means 12, 35 and 36 | Gear pump model 17-51-303 Extraction Sampling Pump, mfg. by Micropump, 1035 Shary Court Concord, Calif. 94518 |
| Sample valve means 14 | High pressure model VIII mfg. by Applied Automation, Inc. Pawhuska Rd., Bartlesville, OK 74004 |
| Valve means 16,17,18, and 19 | Hoke valve No. 7663G4Y mfg. by Hoke Incorporated, Cresskill, N.J. |
| Conduit means 31,32,33, and 34 | Same size or larger than associated conduit means 11 and 21 |
| Pump means 47 | Model MCP-36 mfg. by Haskel Engineering and Supply Co., 100 E. Graham Place Burbank, Calif. 91502 |
| Connecting conduits 41, 42 | 1/4 in. O.D. (2–3 in.) stainless steel or short as possible |
| Carrier fluid supply conduit 45 | 1/6 in. O.D. stainless steel tube |
| Analyzer means 46 | Optichrom L/C liquid chromatographic analyzers sold by Applied Automation, Inc. |
| Programming means 51 | Model 102 sold by Applied Automation, Inc. |

Although the apparatus and method of the invention have been described herein in conjunction with a presently preferred embodiment thereof, it is to be understood that reasonable variations and modifications by those skilled in the art of sampling and analysis of various materials are within the scope of the foregoing description of the invention and of the appended claims thereto.

What is claimed is:

1. Apparatus comprising:
    first conduit means having a passageway therethrough with a first internal volume;
    second conduit means having a passageway therethrough with a second internal volume, said second internal volume having a predetermined size relationship to said first volume;
    means for filling said passageway of said first conduit means with a diluent liquid;
    means for filling said passageway of said second conduit means with a sample material;
    means for connecting said passageway of said first conduit means and said passageway of said second conduit means to form a closed conduit loop; and
    means for circulating said diluent liquid and sample material through said conduit loop to cause mixing thereof.

2. Apparatus in accordance with claim 1 additionally comprising means for removing a preselected volume of diluted sample material from said conduit loop.

3. Apparatus in accordance with claim 1 wherein said means for circulating comprises a pump means.

4. Apparatus in accordance with claim 3 wherein said pump means is associated with said first conduit means.

5. Apparatus in accordance with claim 1 wherein said first and second conduit means comprise tubing having an inside diameter greater than about 0.2 inches.

6. Apparatus in accordance with claim 1 wherein both said first and second conduit means comprise tubing having substantially the same inside diameter.

7. Apparatus in accordance with claim 1 additionally comprising means for analyzing said preselected volume of diluted sample material removed from said conduit loop.

8. Apparatus in accordance with claim 1 wherein said first conduit means has first and second ends and said second conduit means has first and second ends and wherein said means for filling said first conduit means, said means for filling said second conduit means and said means for connecting said first conduit means and said second conduit means comprise:
    first valve means associated with said first end of said first conduit means and having a first position for establishing fluid communication between said first conduit means and a diluent disposal conduit and a second position for establishing fluid communication between said first conduit means and the first end of a first connecting conduit;
    second valve means associated with said first end of said second conduit means and having a first position for establishing fluid communication between said second conduit means and a sample disposal conduit and a second position for establishing fluid communication between said second conduit means and the second end of said first connecting conduit;
    third valve means associated with said second end of said second conduit means and having a first position for establishing fluid communication between said second conduit means and a sample supply conduit and a second position for establishing fluid communication between said second conduit means and the first end of a second connecting conduit;
    fourth valve means associated with said second end of said first conduit means and having a first position for establishing fluid communication between said first conduit means and a diluent supply conduit and a second position for establishing fluid communication between said first conduit and the second end of said second connecting conduit; and
    programming means for automatically placing said first, second, third, and fourth valve means in their respective first positions to fill said first conduit means with said diluent liquid and to fill said second conduit means with said sample material, and for automatically placing said first, second, third and fourth valve means in their respective second positions to connect said first and second conduit means through said first and second connecting conduits to form said conduit loop.

9. Apparatus in accordance with claim 8 wherein said means for circulating comprises a pump means associated with said first conduit means.

10. Apparatus in accordance with claim 9 wherein said first and second conduit means comprise tubing having an inside diameter greater than about 0.2 inches.

11. Apparatus in accordance with claim 10 additionally comprising means for analyzing said preselected volume of diluted sample material removed from said conduit loop.

12. A method for diluting a sample, said method comprising:
   filling a first conduit means with a preselected volume of diluent liquid;
   filling a second conduit means with a preselected volume of sample material;
   combining said first and second conduit means to form a closed conduit loop; and
   circulating said diluent liquid and sample material through said loop until a substantially uniform mixture of diluent and sample within said loop is obtained.

13. A method in accordance with claim 12 wherein circulating said diluent liquid and sample material comprises continuously pumping the contents of said loop in a preselected direction around said loop.

14. A method in accordance with claim 13 wherein said sample material comprises a polymeric material.

15. A method in accordance with claim 13 wherein said sample material comprises a rubber material.

* * * * *